(12) United States Patent
Miller et al.

(10) Patent No.: US 6,900,362 B2
(45) Date of Patent: May 31, 2005

(54) VAPOR PHASE PRODUCTION OF 1,1,1,2,3,3,3-HEPTAFLUOROPROPANE FROM HYDROGEN FLUORIDE AND HEXAFLUOROPROPYLENE

(75) Inventors: Ralph Newton Miller, Newark, DE (US); Mario J. Nappa, Newark, DE (US); Donald J. Toton, New Castle, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/285,193

(22) Filed: Oct. 31, 2002

(65) Prior Publication Data

US 2003/0088132 A1 May 8, 2003

Related U.S. Application Data

(60) Provisional application No. 60/339,923, filed on Oct. 31, 2001.

(51) Int. Cl.$^7$ .......................... C07C 17/00; C07C 19/08; C07C 21/18; C07C 17/08; C07C 23/00
(52) U.S. Cl. ........................ 570/165; 570/134; 570/136; 570/123; 570/124; 570/177; 570/178; 570/166; 570/167; 570/168; 570/169
(58) Field of Search .................. 570/165, 136, 570/134, 124, 123, 177, 178, 166, 167, 168, 169

(56) References Cited

U.S. PATENT DOCUMENTS 5,689,019 A * 11/1997 Aoyama et al. ............. 570/167
6,407,297 B1 * 6/2002 Ewing ........................ 570/178

FOREIGN PATENT DOCUMENTS

| WO | WO 9837043 | 8/1998 |
| WO | WO 9906342 | 2/1999 |
| WO | WO 9926907 | 6/1999 |

* cited by examiner

*Primary Examiner*—Elvis O. Price
(74) *Attorney, Agent, or Firm*—James E. Shipley

(57) ABSTRACT

A process for the production of HFC-227ea from HF and HFP is provided. This process takes advantage of an azeotropic composition of HF and HFC-227ea in order to produce HFC-227ea essentially free of HF and recycle unreacted HF back to the reactor. The recycle of said azeotropic composition, also allows the use of HFC-227ea as a diluent to aid in control of reactor temperature for a highly exothermic reaction.

4 Claims, 1 Drawing Sheet

VAPOR PHASE PRODUCTION OF 1,1,1,2,3,3,3-HEPTAFLUOROPROPANE FROM HYDROGEN FLUORIDE AND HEXAFLUOROPROPYLENE

CROSS REFERENCE TO RELATED APPLICATION

This application claims the priority benefit of U.S. Provisional Application 60/339,923, filed Oct. 31, 2001.

FIELD OF THE INVENTION

The present invention relates to a chemical manufacturing process for the production of 1,1,1,2,3,3,3-heptafluoropropane (HFC-227ea) from hydrogen fluoride (HF) and hexafluoropropylene (HFP).

BACKGROUND

Halocarbons containing chlorine or bromine, in particular chlorofluorocarbons or bromofluorocarbons, have been widely used as solvents, blowing agents, refrigerants, cleaning agents, aerosol propellants, heat transfer media, dielectrics, fire extinguishing agents, and power cycle working fluids. Many of these chlorofluorocarbons and bromofluorocarbons are considered to be detrimental toward the Earth's ozone layer. The worldwide effort to develop materials having lower ozone depletion potential has identified numerous hydrofluorocarbons (i.e. compounds containing only carbon, hydrogen and fluorine) which can serve as effective replacements for chlorofluorocarbons or bromofluorocarbons in the applications listed above. For example, the hydrofluorocarbon 1,1,1,2-tetrafluoroethane (HFC-134a) is being used as a replacement for dichlorodifluoromethane (CFC-12) in refrigeration systems. Another hydrofluorocarbon, 1,1,1,2,3,3,3-heptafluoropropane (HFC-227ea), has been identified as a promising replacement for chlorofluorocarbons or bromofluorocarbons in several applications.

The production of hydrofluorocarbons has been the subject of considerable interest in order to provide environmentally desirable chlorofluorocarbon and bromofluorocarbon alternatives to the market place. The reaction of hydrogen fluoride (HF) and hexafluoropropylene (HFP) is known in the art. However, the highly exothermic reaction requires significant cooling of the reaction zone to prevent overheating of the catalyst. This excess heat can be responsible for the production of undesirable by-products and reduced catalyst lifetime.

The products of the reaction of HF and HFP include HFC-227ea as well as excess HF and HFP. The excess HFP and the other organic impurities can be removed by conventional separation techniques. But recovery of the unreacted HF is difficult due to the formation of a low-boiling azeotrope of HFC-227ea and HF.

It is the object of this invention to provide a process for the production of HFC-227ea which recovers and recycles the excess HF as the azeotropic composition of HF and HFC-227ea and circulates the excess HFC-227ea as a diluent in the system to control the temperature rise in the reaction zone.

SUMMARY OF THE INVENTION

The present invention is directed to a process for producing 1,1,1,2,3,3,3-heptafluoropropane (HFC-227ea) from hydrogen fluoride (HF) and hexafluoropropylene (HFP) said HFC-227ea being essentially free of HF. The improved process utilizes the azeotrope formed by HF and HFC-227ea in order to recycle excess HF and HFC-227ea back to the reactor. This recycle stream reduces waste of HF and provides a diluent (HFC-227ea) which aids in controlling the temperature in the reaction zone for the highly exothermic reaction.

Further, the process preferably operates with a feed ratio of HFC-227ea:HF:HFP of about 5:3:1 and utilizes a fluorination catalyst, such as chromium oxide prepared by pyrolysis of ammonium dichromate.

DETAILED DESCRIPTION

Figure 1:
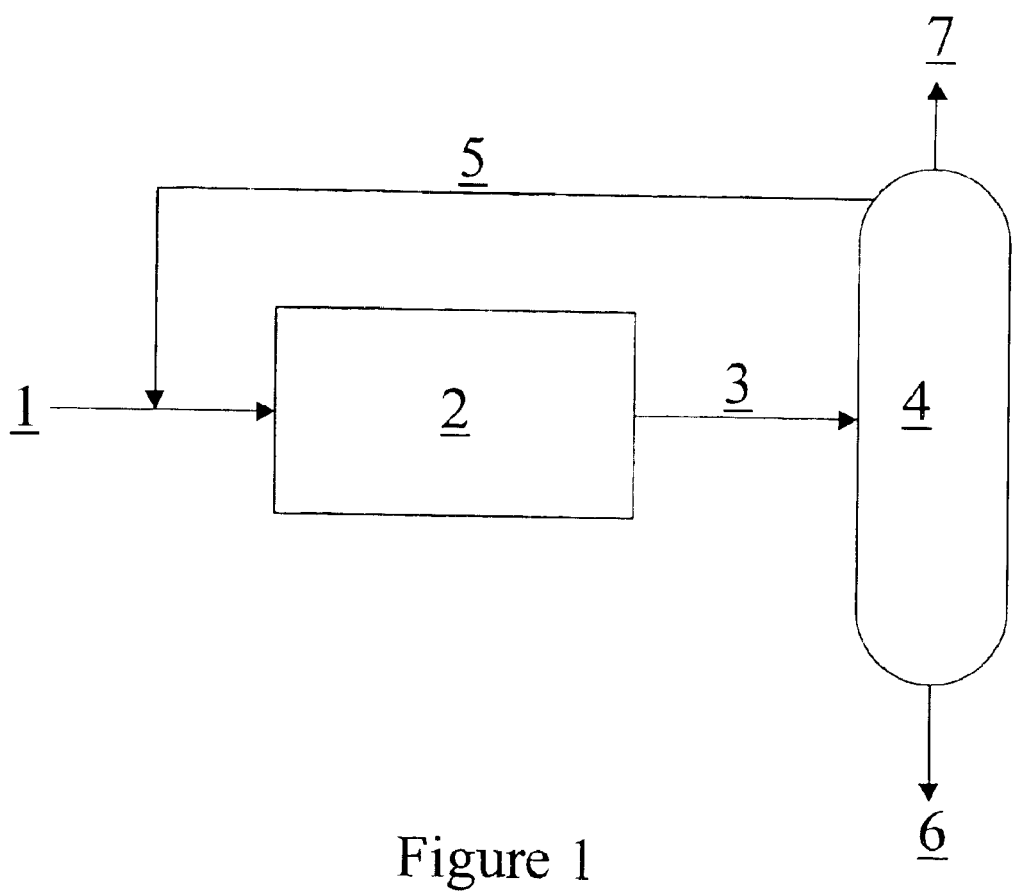
FIG. 1 is a simple schematic representation of a plant, which may be used for carrying out the present process for production of HFC-227ea.

The present invention provides a process for producing 1,1,1,2,3,3,3-heptafluoropropane (HFC-227ea) comprising the steps of: a.) reacting hexafluoropropylene (HFP) and hydrogen fluoride (HF) in the vapor phase in a reaction zone in the presence of HFC-227ea to form a reaction mixture, b.) feeding said reaction mixture to a distillation column to form a distillation column overhead stream comprising HF and HFC-227ea, and a distillation column bottom stream comprising HFC-227ea substantially free of HF, c.) recycling at least a portion of said distillation column overhead stream to said reaction zone, and d.) recovering said distillation column bottom stream comprising HFC-227ea substantially free of HF.

The present process includes the vapor phase reaction of HFP and HF in a reaction zone in the presence of HFC-227ea and forming a reaction mixture comprising HF and HFC-227ea as well as minor amounts of unreacted HFP and reaction by-products including 1,1,1,3,3,3-hexafluoropropane (HFC-236fa), 2-chloro-1,1,1,2,3,3,3-heptafluoropropane (CFC-217ba), 1,1,3,3,3-pentafluoropropene (HFC-1225zc), hexafluoroethane (PFC-116), and octafluoropropane (PFC-218).

The reaction zone may comprise a flow reactor preferably containing a fixed bed of fluorination catalyst. The reactor and associated feed lines, product lines, and associated units contacting HF may be constructed of materials resistant to HF. Typical materials of construction well known in the fluorination field include stainless steels and high nickel alloys, such as Monel® nickel-copper alloys, Hastelloy® nickel-based alloys, and Inconel® nickel-chromium alloys. The reaction of HFP with HF to form HFC-227ea is significantly exothermic (e.g., $\Delta H^{275°\ C.} \approx -29.1$ kcal/mole). It has been discovered that this reaction is preferably carried out in the vapor phase in the presence of a diluent comprising HFC-227ea, which is present in excess of the steady state amount of HFC-227ea formed in the reaction zone. Preferably, the HFC-227ea diluent fed to the reaction zone is an azeotropic or azeotrope-like composition of HFC-227ea and HF. Under the reaction conditions, HFC-227ea is stable and negligible reverse reaction to HFP and HF occurs. HFC-227ea added to the reaction zone as a diluent absorbs thermal energy arising from the significantly exothermic reaction of HFP and HF. Removal of this thermal energy and control of the temperature rise across the reactor is thus achieved by controlling the amount of diluent HFC-227ea fed to the reaction zone. Excessive temperature rise across the reactor is undesirable and shortens the life of the fluorination catalyst as well as increases the potential for the formation of undesirable by-products (e.g., HFC-236fa, CFC-217ba, HFC-1225zc, PFC-hexafluoroethane, and PFC-218). The present process allows for the reaction to be carried out in an adiabatic reactor or series of adiabatic reactors. Adiabatic reactors are reactors to which none, or little, additional heating or cooling is required. Optionally, external cooling of the reactor can be supplied to further minimize temperature rise, thus allowing for higher throughput of reactants through the reaction zone.

The present vapor phase reaction of HFP with HF to form HFC-227ea is preferably carried out in the presence of a fluorination catalyst. Fluorination catalysts of utility in this reaction include: (i) those based on metal oxides/halides or oxyhalides or mixed metal oxides/halides/oxyhalides for example chromia and alumina; (ii) those based on other metal oxides/halides/oxyhalides supported on chromia or alumina, for example oxides of zinc, iron, magnesium or nickel; and (iii) those based on metal oxides/halides/oxyhalides, or mixed metal oxides/halides/oxyhalides supported on carbon. A preferred fluorination catalyst is a chromium oxide catalyst prepared by the pyrolysis of ammonium dichromate as taught in U.S. Pat. No. 5,036,036, herein incorporated by reference. The fluorination catalyst may be granulated, pressed into pellets, or shaped into other desirable forms and contained in the reactor in a variety of fashions generally known in the art, e.g., a packed bed of fluorination catalyst in a flow reactor. The catalysts may be given a prefluorination treatment by passing HF, with or without an inert diluent such as nitrogen, over the catalyst at a temperature within the range of about 250 to 450° C. prior to use. After use for a period of time, the activity of the fluorination catalyst may decrease. When this occurs, the fluorination catalyst may be reactivated by treatment with oxygen or air at elevated temperature in the absence of organic materials.

The HFP and HF reaction may be initiated by heating the HFP and HF prior to feeding them to the reactor zone or by heating the reaction zone in the region where the HFP and HF are fed to the reactor. The temperature of the reaction zone during the reaction of HFP and HF in the presence of a fluorination catalyst may be maintained at between about 180° C. to about 300° C., preferably from about 200° C. to about 250° C., by controlling the amount of diluent comprising HFC-227ea present in the reaction zone. The pressure in the reaction zone is not critical and may be from atmospheric to superatmospheric, normally from about 0 psig to about 250 psig, preferably from about 50 psig to about 150 psig. The contact time of the vapor phase in the reaction zone with fluorination catalyst (i.e., the volume of the catalyst bed divided by the volumetric flow rate at the preferred temperature of, and preferred pressure in, the reaction zone) is not critical and is typically from about 2 seconds to about 8 minutes, preferably about 15 seconds. The quantity of HFP fed to the reaction zone is generally between about 0.06 to about 0.40 (lb. HFP fed/hour)/lb. fluorination catalyst, and preferably about 0.25 (lb. HFP fed/hour)/lb. fluorination catalyst when the fluorination catalyst is the preferred chromium oxide catalyst. Using the preferred reaction conditions, the conversion of HFP may be at least about 95% and the yield of HFC-227ea from HFP may be at least about 99%.

The mole ratios of HFP, HF and diluent HFC-227ea fed to the reaction zone are from about 2:1 to about 4:1 HF:HFP, and from about 2:1 to about 8:1 HFC-227ea:HFP, preferably about 3:1 HF:HFP and about 5:1 HFC-227ea:HFP. It is a surprise to find out that under conditions described in this invention, increasing HF:HFP ratio will decrease the conversion rate of HFP. For instance, in one experiment, when HF:HFP ratio was 2.23, the HFP conversion rate was 99.55%. However, in another experiment, when other conditions were essentially the same and the HF:HFP ratio was increased to 6.18, the HFP conversion rate decreased to 87%.

The present process includes distilling the reaction mixture obtained from the reaction zone to form a distillation column overhead stream comprising HF and HFC-227ea, and a distillation column bottom stream comprising HFC-227ea substantially free of HF.

The reaction mixture obtained from the reaction zone comprises HF and HFC-227ea as well as minor amounts of unreacted HFP (e.g., less than about 1 mole %) and reaction by-products (e.g., less than about 5 mole %) including HFC-236fa, CFC-217ba, HFC-1225zc, PFC-116, and PFC-218. This vapor stream may be cooled and condensed or compressed to form a liquid phase to be fed to the distillation step of the present invention.

A low-boiling azeotropic or azeotrope-like composition boils at a lower temperature at any given pressure than any one of the compounds that comprise it would separately boil at that pressure. Alternately, a low-boiling azeotrope has a higher vapor pressure at any given temperature than the vapor pressure of any one of the compounds that comprise the azeotrope would separately have at that temperature. WIPO PCT publication WO 98/37043 discloses low boiling azeotropic and azeotrope-like compositions of HF and HFC-227ea consisting essentially of from about 29.9 to about 41.3 mole percent HF and from about 70.1 to 58.7 mole percent HFC-227ea, said composition having a boiling point from about −25° C. at 78 kPa to about 100° C. at 3764 kPa. WIPO PCT publication WO 99/26907 discloses an azeotropic composition of HF and HFP. At 174 psi the HFP/HF azeotrope is reported to have a boiling point of 98° F. (37° C.) and contains 38 mole percent HF and 62 mole percent HFP.

At constant pressure, the boiling point of the HFP/HF azeotrope is lower than that of the HFC-227ea/HF azeotrope which is lower than the boiling points of any of the pure components HF, HFC-227ea and HFP. When the present reaction mixture is distilled, the lowest boiling components in the reaction mixture such as PFC-116, HFP, PFC-218 as well as the low boiling azeotrope of HF/HFC-227ea are removed as overhead streams from the distillation column. The mole ratio of HFC-227ea:HF:HFP fed to the reaction zone may preferably be about 5:3:1. HFP forms HFC-227ea in high conversion and yield in the reaction and the mole ratio of HFC-227ea:HF in the reaction mixture may be thus about 3:1. As the mole ratio of HFC-227ea:HF in the HFC-227ea/HF azeotropic or azeotrope-like composition ranges from about 1.4:1 to 2.3:1 depending on the conditions, the distilling step of the present process leads to removal of substantially all HF from the reaction mixture as a distillation column overhead stream comprising HF and HFC-227ea. The HFC-227ea present in the reaction mixture in excess of the amount of HFC-227ea in the HFC-227ea/HF azeotropic or azeotrope-like composition is recovered from the distillation step as a distillation column bottom stream comprising HFC-227ea substantially free of HF.

In the distillation step, the overhead stream exiting the distillation column comprising HF and HFC-227ea may be condensed using conventional reflux condensers. At least a portion of this condensed stream may be returned to the top of the column as reflux, and the remainder recycled to the reaction zone. The ratio of the condensed material which is returned to the top of the distillation column as reflux to the material removed as distillate is commonly referred to as the reflux ratio. The specific conditions which may be used for practicing the distillation step of the present invention depend upon a number of parameters, such as the diameter of the distillation column, feed points, number of separation stages in the column, among others. The operating pressure of the distillation column may range from about 50 to about 250 psia, normally about 100 psia to about 150 psia. The distillation column is typically operated at a pressure of about 115 psia with a bottoms temperature of about 44° C. and a tops temperature of about 37° C. Normally, increasing the reflux ratio results in increased distillate stream purity, but generally the reflux ratio ranges between 1/1 to 200/1. The temperature of the condenser, which is located adjacent to the top of the column, is normally sufficient to substantially fully condense the distillate that is exiting from the top of the column, or is that temperature required to achieve the desired reflux ratio by partial condensation.

The present process includes recycling at least a portion of the distillation column overhead stream comprising HF and HFC-227ea to the reaction zone. The distillation column overhead stream comprises an azeotropic or azeotrope-like composition of HF and HFC-227ea. The distillation column overhead stream may be recycled to the reaction zone, provided that the mole ratio of HFP, HF and HFC-227ea fed to the reaction zone may be about 5:3:1 HFC-227ea:HF:HFP.

The present process includes recovering a distillation column bottom stream comprising HFC-227ea substantially free of HF. By HFC-227ea substantially free of HF is meant HFC-227ea containing less than about 1,000 weight ppm HF, preferably less than about 10 weight ppm HF.

EXAMPLE

The present invention is now further exemplified by reference to FIG. 1, which is a simple schematic representation of a plant, which may be used for carrying out the present process. In FIG. 1, HF and HFP are vaporized and fed (1) to a vapor phase, catalytic reactor (2) operating at 50 psig and 200–300° C. Also fed to the reactor is a recycle diluent (5) comprising a distillation column overhead stream of HF and HFC-227ea. The mole ratio of HFC-227ea:HF:HFP (from the combination of 1 and 5 streams) fed to the reactor (2) is maintained at about 5:3:1 HFC-227ea:HF:HFP. The reactor (2) inlet temperature is maintained at 200° C. By adjusting the flow rate of the diluent stream (5), the temperature rise across the reactor (2) is controlled and a high conversion (95%) of HFP is achieved. The reaction mixture comprising HF and HFC-227ea is condensed and fed (3) to a distillation column (4) operating from 50 to 150 psig. HF and HFC-227ea form a low-boiling azeotrope and substantially all of the HF and an azeotropic amount (or more) of HFC-227ea exit the distillation column as an overhead stream and are recycled (5) as a diluent to the reactor (2). Low-boiling by-products, such as PFC-218, exit the distillation column as an overhead stream (7). The distillation column bottoms stream (6) comprises HFC-227ea substantially free of HF. High-boiling by-products, such as HFC-236fa, exit the distillation column along with the product HFC-227ea in stream (6).

Table 1 illustrates the flow of components through a process as illustrated in FIG. 1. The calculation was completed assuming 100 lbs of HFP being fed and the pressure at all points of the process being the same, 50 psig (64.7 psia). The HF:HFP feed mole ratio is 3.45:1 and the 227ea:HFP feed mole ratio is 4.29:1. This data demonstrates that the product HFC-227ea in stream (6) is essentially free of HF as expected. The path of both by-products, the higher-boiling HFC-236fa and the lower-boiling PFC-218, is such that minimization is highly desirable. Over time, both will accumulate in the reactor/recycle loop and limit the overall purity obtained. Also, the presence of substantial amounts of high-boiling by-products in the column bottom stream (6) will require additional separation equipment. Thus, maintaining the temperature as low as possible with the use of the diluent to minimize by-product formation is essential to this process.

TABLE 1

| Flow (moles) | 1<br>Reactor Feed<br>(HFP + HF,<br>make-up) | 3<br>Reaction<br>Mixture<br>(227ea + HF) | 5<br>Recycle<br>Diluent<br>(227ea + HF) | 6<br>Column<br>Bottoms<br>(227ea) | 7<br>Column<br>Overhead<br>(Inerts) |
|---|---|---|---|---|---|
| HF | 0.675 | 1.732 | 1.725 | $1.70 \times 10^{-8}$ | 7.25 |
| HFP | 0.667 | 0.0292 | 0.0293 | $3.14 \times 10^{-5}$ | $1.54 \times 10^{-4}$ |
| 227ea | 0.0 | 3.642 | 2.981 | 0.651 | 0.0010 |
| 218 | 0.0 | 0.404 | 0.401 | $4.88 \times 10^{-7}$ | 0.00333 |
| 236fa | 0.0 | 0.00429 | 0.00207 | 0.00221 | $4.90 \times 10^{-6}$ |
| Temp (° C.) | 135 | 298 | 17.7 | 24.8 | 12.4 |
| Pres (psia) | 64.7 | 64.7 | 64.7 | 64.7 | 64.7 |

What is claimed is:

1. A process for producing HFC-227ea, comprising:
   a.) reacting HFP and HF in the vapor phase in a reaction zone in the presence of HFC-227ea and a fluorination catalyst to form a reaction mixture, wherein said HFP, HF and HFC-227ea are added to said reaction zone in a mole ratio from about 2:1 to about 3:1 HF:HFP and a mole ratio of about 5:1 HFC-227ea:HFP,
   b.) feeding said reaction mixture to a distillation column to form a distillation column overhead stream comprising HF and HFC-227ea, and a distillation column bottom stream comprising HFC-227ea substantially free of HF,
   c.) recycling at least a portion of said distillation column overhead stream to said reaction zone, and
   d.) recovering said distillation column bottom stream comprising HFC-227ea substantially free of HF.

2. The process of claim 1 wherein the temperature of said reaction zone is from about 200° C. to about 250° C.

3. The process of claim 1 wherein said fluorination catalyst comprises chromium oxide prepared by pyrolysis of ammonium dichromate.

4. The process of claim 1 wherein said distillation column overhead stream comprises an azeotropic or azeotrope-like composition consisting essentially of HF and HFC-227ea.

* * * * *